US010040833B2

(12) United States Patent
Sliekers et al.

(10) Patent No.: US 10,040,833 B2
(45) Date of Patent: Aug. 7, 2018

(54) NISIN PRODUCTION PROCESS

(71) Applicant: Purac Biochem B.V., Gorinchem (NL)

(72) Inventors: Arne Olav Sliekers, Breda (NL); Jasper Meijer, Breda (NL); Diana Visser, Haarlem (NL)

(73) Assignee: PURAC BIOCHEM B.V., Gorinchem (NL)

( * ) Notice: Subject to any disclaimer, the term of this patent is extended or adjusted under 35 U.S.C. 154(b) by 289 days.

(21) Appl. No.: 14/760,981

(22) PCT Filed: Jan. 15, 2014

(86) PCT No.: PCT/NL2014/050016
§ 371 (c)(1),
(2) Date: Jul. 14, 2015

(87) PCT Pub. No.: WO2014/112871
PCT Pub. Date: Jul. 24, 2014

(65) Prior Publication Data
US 2015/0353611 A1    Dec. 10, 2015

Related U.S. Application Data

(60) Provisional application No. 61/752,584, filed on Jan. 15, 2013.

(30) Foreign Application Priority Data

Jan. 15, 2013   (EP) ..................... 13151293

(51) Int. Cl.
| C12N 1/20 | (2006.01) |
| A23C 9/123 | (2006.01) |
| C07K 14/335 | (2006.01) |
| A23L 3/3544 | (2006.01) |
| A23L 3/3463 | (2006.01) |
| C07K 14/315 | (2006.01) |
| A23L 3/3526 | (2006.01) |
| A23L 3/3571 | (2006.01) |

(52) U.S. Cl.
CPC ........ *C07K 14/335* (2013.01); *A23L 3/34635* (2013.01); *A23L 3/3526* (2013.01); *A23L 3/3544* (2013.01); *A23L 3/3571* (2013.01); *C07K 14/315* (2013.01); *A23V 2002/00* (2013.01)

(58) Field of Classification Search
None
See application file for complete search history.

(56) References Cited

U.S. PATENT DOCUMENTS

| 2,143,361 A | 1/1939 | Morgan et al. |
| 2,222,520 A | 11/1940 | Sturm |
| 2,856,326 A | 10/1958 | Shaw |
| 5,274,152 A | 12/1993 | Carmody |
| 5,716,811 A | 2/1998 | Nauth et al. |
| 6,110,509 A * | 8/2000 | Nauth ............... A23C 19/062 426/41 |
| 7,186,426 B2 * | 3/2007 | Nauth .................. C12C 5/00 426/16 |
| 2002/0192331 A1 * | 12/2002 | Nauth .................. C12C 5/00 426/16 |
| 2005/0013901 A1 * | 1/2005 | Glass ................. A23C 21/02 426/41 |
| 2005/0287272 A1 | 12/2005 | Zheng et al. |
| 2008/0125488 A1 | 5/2008 | Leverve et al. |
| 2008/0152758 A1 | 6/2008 | Zheng et al. |
| 2008/0152764 A1 | 6/2008 | Kremer et al. |
| 2010/0062503 A1 | 3/2010 | Visser et al. |
| 2011/0300220 A1 | 12/2011 | Coszach et al. |

FOREIGN PATENT DOCUMENTS

| EP | 1 797 773 A1 | 6/2007 |
| JP | 63-225332 | 9/1988 |
| JP | 2502572 B2 | 5/1996 |
| WO | WO-00/28973 A1 | 5/2000 |
| WO | WO-03/031385 A1 | 4/2003 |

(Continued)

OTHER PUBLICATIONS

De Vuyst, et al., "Nisin, A lantibiotic produced by *Lactococcus lactis* subsp. lactis: properties, biosynthesis, fermentation and applications" in: De Vuyst, L. et al: Bacteriocins of lactic acid bacteria, Chapman Hall (1994) Chapter 5, pp. 151-221.
International Search Report of PCT/NL2014/050014 dated Mar. 21, 2014.
International Search Report of PCT/NL2014/050015 dated Mar. 21, 2014.
International Search Report of PCT/NL2014/050016 dated Mar. 21, 2014.
Kalra, et al., "Effect of calcium carbonate on nisin production in a milk culture", Indian Journal of Dairy Science, (1973) vol. 261-15, pp. 146-148.
Perez-Guerra, N. et al., "Production of bacteriocins from *Lactococcuslactis* subsp. lactis CECT 539 and pediococcus acidilactici NRRL B-5627 using mussel-processing wastes", Biotechnology and Applied Biochemistry (2002) vol. 36, No. 2, pp. 119-125.

(Continued)

*Primary Examiner* — Chris R Tate
*Assistant Examiner* — Douglas F White
(74) *Attorney, Agent, or Firm* — Gilberto M. Vilacorta; Sunit Talapatra; Foley & Lardner LLP (57) ABSTRACT

The present invention relates to fermentation processes. The objective of the invention was to provide methods for producing nisin containing ferments and formulating such ferments into preservatives. It was in particular an object of the present invention to provide improved processes for producing nisin containing ferments by simple and efficient (batch) culturing and allowing for simple down-stream processing either into a liquid, semi-liquid or a dry powder product, having sufficient nisin content and stability, good handling properties and satisfactory organoleptic properties. Such processes are provided, as well as the products that can be obtained with it and their use.

12 Claims, 2 Drawing Sheets

(56) References Cited

FOREIGN PATENT DOCUMENTS

WO    WO-2010/111680 A2    9/2010
WO    WO-2012/030664 A1    3/2012

OTHER PUBLICATIONS

Van'T Hul, et al., "Neutralization/recovery of lactic acid from Lactococcus lactis: effects on biomass, lactic acid, and nisin production", World Journal of Microbiology and Biotechnology (1997) vol. 13, No. 5, pp. 527-532.

"Purasal P HiPure 60 Specification", Internet Citation, Sep. 19, 2002, XP002213995, retrieved from the Internet: URL:http://www.purac.com/products/EN-PHiPure60NPL.PDF.

* cited by examiner

Figure 1:
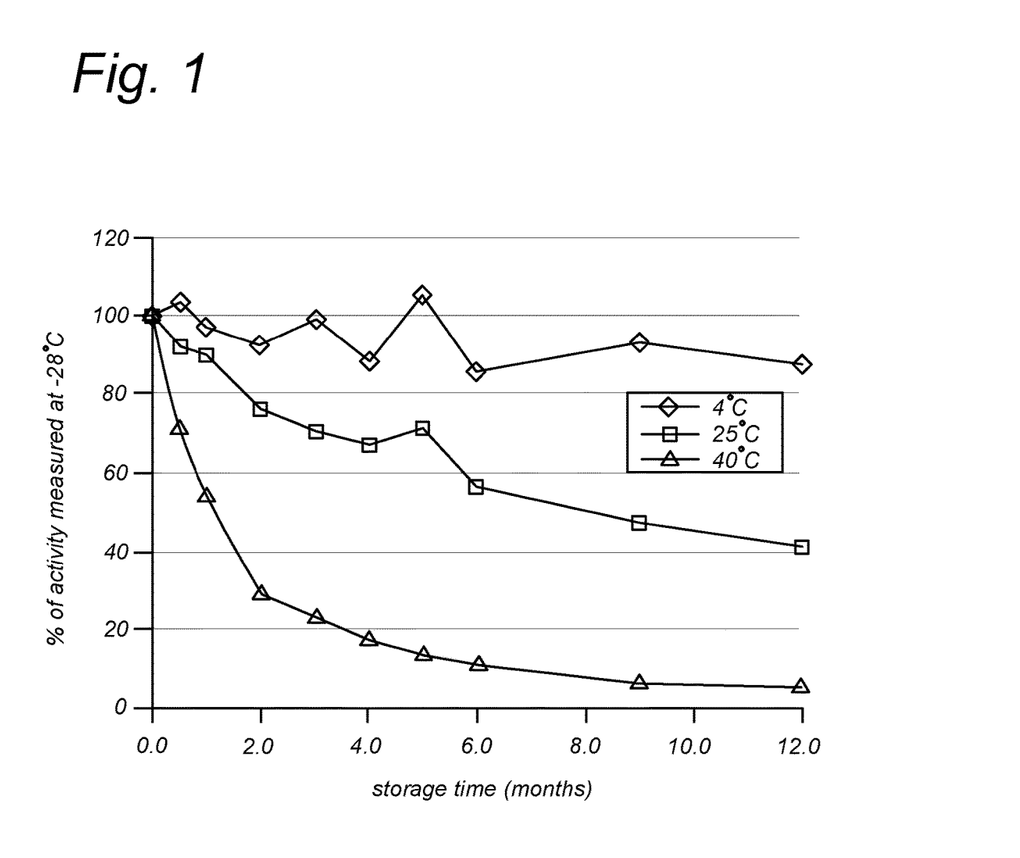

*Fig. 1*

Fig. 2

NISIN PRODUCTION PROCESS

CROSS REFERENCE TO RELATED APPLICATIONS

The present application is a National Stage of International Application No. PCT/NL2014/050016 filed on Jan. 15, 2014, which was published on Jul. 24, 2014, as WO 2014/112871 A1, and which claims the benefit of U.S. Application No. 61/752,584 filed Jan. 15, 2013, and which claims the benefit of EP Application No. 13151293.1 filed Jan. 15, 2013, the entire disclosures of which are incorporated herein by reference.

FIELD OF THE INVENTION

The present invention relates to fermentation processes. More in particular, an improved method is provided for the production of lactic acid ferments, which also contain nisin.

BACKGROUND OF THE INVENTION

To prevent decay and quality deterioration of food products, preservatives are commonly added. For decades, chemically synthesized food preservatives have been the primary choice to achieve this goal. More recently, safety issues have been raised with respect to these chemically synthesized food preservatives. Ever since, there has been a growing interest in antimicrobial substances derived from traditional foods.

Lactic acid bacteria are useful microorganisms, which have been traditionally used in the production of various fermented food products. Lactic acid fermentation results in inhibition of the growth of other contaminating bacteria. Due to the pH reduction of the systems with lactic acid produced via lactic acid fermentation, decay and quality deterioration of such food products can be prevented and/or reduced. Additionally, it has been determined that certain additional antimicrobial substances, such as bacteriocins, are produced by some lactic acid bacteria. A known bacteriocin for the control of pathogens in food is nisin. Nisin is produced by *Lactococcus lactis* strains and inhibits a broad range of Gram-positive bacteria. These bacteriocins belong to the lantibiotics group (class I bacteriocins) and have a long history as food preservative.

It is becoming increasingly common to use lactic acid and nisin containing ferments produced by such strains as preservative agents in all kinds of food products.

Conventional bacteriocin fermentation methods are generally inefficient for nisin production on a large (commercial) scale due to limited production rates and unsatisfactory final nisin concentrations. Prolonging the fermentation process also inherently increases the risks of contamination of production batches. More importantly, slow nisin production rates make commercial nisin production costly. Another relevant cost factor is the relatively expensive fermentation medium requirements.

Nisin containing ferments are only exceptionally produced at the same plant where they are also applied to produce the final food products. In most instances nisin containing ferments will be manufactured at one plant to be used, typically some time later, at another plant in the production of the food product. The fermentation products therefore often need to be processed into formulations that can be stored for some time without loss of quality and/or activity, can be transported efficiently and are convenient to handle and to dose in the production of food products. Often, for this purpose, ferments are formulated as a dry powder. Such powdered ferment products however have several drawbacks: dust is generated upon handling, and dosing and mixing small amounts of powders into products is difficult. Liquid preservative compositions are therefore sometimes preferred.

The possibilities of producing stable and easy-to-use liquid and semi-liquid formulations of nisin containing ferments are to a large extent determined by the thermodynamic behavior of the lactic acid salt(s), constituting the bulk of the ferment. This thermodynamic behavior sets the conditions required for downstream processing into the formulation type of choice, which conditions in turn may have significant impact on the nisin content/activity in the formulation.

Last but not least, organoleptic, dietary and food regulatory requirements additionally put restraints on the fermentation and down-stream processing steps and the types and amounts of the materials to be used therein.

In summary, manufacturers of nisin containing preservative compositions encounter a number of interrelated technological challenges to optimize the process and satisfy the needs and requirements imposed by specific (end-)uses of the product, in particular with regard to production rate and yield, stabilization of the activity, and the processing into stable and easy-to-use formulations. As will be understood, keeping the manufacturing costs at an acceptable level is always a factor in the design of the process.

It is an object of the invention to provide methods for producing nisin containing ferments and formulating such ferments into preservatives. It is in particular an object of the present invention to provide improved processes for producing nisin containing ferments by simple and efficient (batch) culturing and allowing for simple down-stream processing into a liquid or semi-liquid product, having sufficient nisin content and stability, good handling properties and satisfactory organoleptic properties.

SUMMARY OF THE INVENTION

The present invention provides a process of producing a nisin containing lactate ferment comprising the consecutive steps of:
a) providing a nutrient medium comprising a solution of a fermentable substrate and a nitrogen source in an aqueous medium;
b) inoculating said nutrient medium with nisin producing lactic acid bacteria; and
c) incubating the inoculated nutrient medium under conditions favorable to the growth and/or metabolic activity of said nisin producing lactic acid bacteria, for a period sufficient to produce a fermentation broth containing at least 10 g/l of lactate equivalents and/or at least 1000 IU/ml of nisin equivalent activity, during which period the pH of the fermentation broth is controlled by addition of an alkalization agent comprising an alkaline potassium salt.

Unexpectedly, the present inventors observed that the use of potassium hydroxide as a neutralizing agent, has certain particular advantages as will become apparent to those skilled in the art on the basis of the description and examples hereafter In one embodiment of the invention, the use of specific activated lactic acid ferments as the inoculation medium is provided, as will be explained and illustrated in more detail here after, to improve the rate and efficiency of the fermentation process.

Furthermore, in an advantageous embodiment of the invention the process comprises the additional step d1) of acidification of the fermentation broth by the addition of an acid, preferably lactic acid, in an amount sufficient to reduce the pH of the fermentation broth to below 4.8.

In an advantageous embodiment of the invention, the process comprises the additional step d2) of inactivating the lactic acid bacteria by subjecting the fermentation broth to a temperature of at least 40° C. for a period of at least 10 minutes.

In an advantageous embodiment of the invention the process comprises the additional step e) of concentrating the ferment obtained in step c) or d) to a dry solids content of at least 50 wt. %, for example by evaporation. The present process yields a product comprising lactate mainly in the form of potassium lactate. Potassium lactate containing ferments proved to allow for concentration to particularly high lactate contents while maintaining the lactate in solution, resulting in a physically stable concentrated liquid product that is easy to handle.

In an advantageous embodiment of the invention the process comprises the additional step f) of cooling the concentrate obtained in step e) to a temperature of below 40° C.

In an advantageous embodiment of the invention, the fermentation broth comprises a dairy base. The present inventors established that satisfactory liquid preservative products can be produced by fermentation of a dairy base in accordance with the invention, without having to apply down-stream clarification/purification operations.

The present invention also provides the ferments and ferment products obtainable by the above-described method and their various applications as preservatives.

These and other aspects and embodiments of the invention will become apparent to those skilled in the art on the basis of the following detailed description and the experimental work described in the subsequent section.

DETAILED DESCRIPTION OF THE INVENTION

As stated herein, the first step a) of the process comprises the preparation of a nutrient medium. In this document, the term "nutrient medium" is used to refer to media in the form originally provided for fermentation. The nutrient medium supplies the substrates and the nutrients the lactic acid bacteria need to grow and to produce the various fermentation products. The nutrient medium typically is an aqueous medium comprising a fermentable substrate, a nitrogen source and micronutrients, wherein the lactic acid bacteria can grow and reproduce. In principle any combination of a carbon source, a nitrogen source and micronutrients may be used as long as it promotes the growth of the lactic acid bacteria.

The term 'fermentation broth' is used herein to refer to the nutrient medium after inoculation with the lactic acid bacteria. Thus, strictly speaking, several types of "fermentation broths" can be distinguished based on the stage to which the fermentation has progressed: (i) nutrient media in the form originally provided including bacteria directly after inoculation; (ii) nutrient media undergoing fermentation wherein some or most of the originally provided nutrients has already been consumed and fermentation products including lactate have been excreted into the media by the bacteria; and, (iii) media that have been removed from the fermentor after part or all of the nutrients have been consumed.

As used herein, the term "fermentable substrate" refers to the carbon source that is converted into another compound by the metabolic action of lactic acid bacteria. As a carbon source, mono-, di-, tri-, oligo and polysaccharides can be used, in particular sugars such as glucose, sucrose, fructose, galactose and lactose and/or starch (hydrolysates). Preferably, in this invention, the substrate is a carbohydrate selected from the group consisting of lactose, sucrose and glucose, most preferably lactose.

These carbohydrates can be derived from a variety of sources, such as dairy products and plant, fruit or vegetable derived products, e.g. molasses, fruit or vegetable juices, fruit or vegetable pulp, etc. The invention can be practiced using one or more carbohydrates in partly or substantially purified form. Alternatively, the invention can practiced using a raw material containing one or more carbohydrates.

The nutrient medium typically contains at least 1 g/l, more preferably 5-300 g/l, most preferably 10-80 g/l, of the carbohydrate.

Suitable examples of nitrogen sources include plant derived protein, such as soy protein and pea protein, dairy protein, yeast or yeast extract, meat extract, various kinds of fermentation fungi, as well as hydrolysates of any of the afore mentioned proteins. It is preferred that the nitrogen source comprises free amino acids and/or short peptides. Suitable nitrogen sources may be prepared by hydrolysing a protein source. In one embodiment of the invention the nitrogen source is selected from the group consisting of yeast extracts and dairy protein hydrolysates, especially casein hydrolysate.

The nutrient medium typically contains at least 0.1 g/l, more preferably 0.2-50 g/l, most preferably 0.5-20 g/l of the nitrogen source. These amounts refer to the total dry solids weight of the material added as the nitrogen source per liter of nutrient medium, as will be understood by those skilled in the art. Hence, the nutrient medium typically contains at least 0.1 g/l, more preferably 0.2-50 g/l, most preferably 0.5-20 g/l of proteins, peptides and/or free amino acids.

In some embodiment of the invention, the nutrient medium further comprises micronutrients that support the growth metabolic action of the lactic acid bacteria, such as vitamins, minerals, co-factors and/or other trace-elements. The micronutrients are generally used at a rate of at least 0.01% (w/v), preferably at a rate of between 0.1 and 2% (w/v) in the nutrient medium. Typically, the carbohydrate sources and/or nitrogen sources that may be used in accordance with the invention inherently contain micronutrients.

A particularly preferred embodiment of the invention concerns the fermentation of a dairy base, i.e. a nutrient medium comprising as a main component a dairy product. As used herein, the term "dairy product" refers to whole (animal) milk, components of the milk as well as products derived from milk, such as whey, whey permeate, milk permeate, yoghurt and quark and by-products from the preparation of yoghurt and quark. In some preferred embodiments, by volume, the major component of the nutrient medium is the dairy product. In some embodiments, the nutrient medium comprises at least 80%, at least 90%, at least 95%, at least 99%, or at least 99.9% of the volume of milk, e.g. a product selected from whole milk, raw milk, skim milk, reconstituted milk, condensed milk, re-hydrated milk and the like. In some embodiment, the nutrient medium comprises at least 80%, at least 90%, at least 95%, at least 99%, or at least 99.9% of the dry solids weight of milk solids, e.g. whole milk solids, raw milk solids, skim milk solids, whey and the like. In a particularly preferred embodiment said milk solid is whey.

Another preferred embodiment of the invention concerns the fermentation of a fruit or vegetable derived product, such as fruit or vegetable derived juices, pastes or pulp. In some preferred embodiments, by volume, the major component of the nutrient medium is the fruit or vegetable derived product. Suitable examples include tomato, carrot, spinach, molasses, etc. In a particularly preferred embodiment of the invention the fruit or vegetable derived product is a juice obtained by mechanically squeezing or macerating the raw fruit or vegetable. In some embodiments, the fruit or vegetable derived product comprises at least 80%, at least 90%, at least 95%, at least 99%, or at least 99.9% of the volume of the nutrient medium. In some embodiments, the nutrient medium comprises at least 80%, at least 90%, at least 95%, at least 99% of the dry solids weight of fruit or vegetable solids.

As stated herein, the subsequent step b) comprises inoculating the nutrient medium with nisin producing lactic acid bacteria, preferably with an inoculation medium comprising a ferment containing activated nisin producing lactic acid bacteria.

In accordance with this invention, the "lactic acid bacteria" are capable of producing nisin. In some preferred embodiments, the lactic acid bacteria belong to the order Lactobacillales, preferably to the *Lactococcus* genus. The lactic acid bacteria producing nisin most preferably belong to *Lactococcus lactis* ssp. *lactis*, and examples thereof include JCM 7638, ATCC 11454, NCDO 497 and IFO 12007. In preferred embodiments, the lactic acid bacteria are lactic acid bacteria that have GRAS status.

In some embodiments, the fermentation broth comprises a single species of nisin producing lactic acid bacteria, while in other embodiments, the fermentation broth comprises a mixture of lactic acid bacteria strains, at least one of which is capable of producing nisin. In one embodiment mixtures of nisin producing lactic acid bacteria strains are used.

In accordance with an embodiment of the invention, the inoculation medium comprises a broth containing activated nisin producing lactic acid bacteria. The term 'activated' is used herein to indicate that the composition used to inoculate the nutrient medium comprises lactic acid bacteria in a metabolically active state. When the bacteria are introduced into the nutrient medium during direct seeding i.e. in the form of a dry, liquid or frozen concentrate, the bacteria do not take effect straight away and require time to become active. This 'time lag', also referred to as lag phase', may involve re-establishment of the stored bacteria into the natural form (rehydration phase of the bacteria), restoration of the metabolic activity and/or adaptation to the new environment. Furthermore, it has been established by the inventors that the use of alkaline potassium salts as an alkalization agent during fermentation negatively affects the fermentation rate. It has been found that the use of specific activated lactic acid bacteria compositions counteracts this effect. Hence, as stated above, in a preferred embodiment of the invention the inoculation of the (production) nutrient medium is done with a fermentation broth comprising activated lactic acid bacteria, typically to shorten the lag phase, which can significantly decrease the overall fermentation time, and/or to increase the rate of reproduction during the exponential phase and/or the rate of lactic acid and/or nisin production during the exponential and/or stationary phases of the fermentation process.

In one embodiment of the invention, a fermentation broth comprising activated lactic acid bacteria is used for inoculating the nutrient medium, wherein the broth comprises more than 12 g/l of lactate equivalents, more preferably more than 14 g/l, most preferably more than 16 g/l. As used herein, the term "lactate equivalent" refers to the total of the free lactic acid and the conjugated base (dissociated acid), as will be understood by those of ordinary skill. The terms "lactic acid" and "free lactic acid" are employed interchangeably herein to refer to the acid form, the term lactate refers to the dissociated form of lactic acid. The (dissolved) salt of lactate is also specifically referred to herein as "lactate salt".

In one embodiment of the invention, the fermentation broth comprising activated lactic acid bacteria used for inoculating the nutrient medium is prepared by incubating the lactic acid bacteria in an activation medium, which is similar in composition to the production nutrient medium. In one embodiment of the invention, the activation medium has the same composition as the production nutrient medium. In one particularly preferred embodiment of the invention, the activation medium is enriched as compared to the production nutrient medium, preferably one or more nutrients applied in the production nutrient medium are used in excess amounts in the activation medium, typically meaning that the concentration is at least 125% of the concentration employed in the nutrient medium. More preferably the activation medium comprises one or more of said nutrients in concentrations of at least 150%, at least 175%, at least 200%, at least 250% or at least 300% of the concentrations employed in the production nutrient medium. In a particularly preferred embodiment of the invention the nitrogen source is used in excess amounts in the activation medium.

As will be understood by those skilled in the art the fermentation broth comprising activated lactic acid bacteria can be prepared using standard equipment and methodology.

As stated herein, the process comprises a step c), wherein the inoculated nutrient medium is incubated to produce a fermentation broth comprising lactate and nisin. Production-scale lactic acid fermentation requires strict control of fermentation conditions, in particular of the pH. Without control of the pH, the formation of lactic acid as a product of the metabolic action of the lactic acid producing bacteria, the pH will decrease as the fermentation proceeds. A drop in pH below a critical value, depending on the microorganism used in the process, could negatively affect the microorganism's metabolic process and eventually bring the fermentation process to a stop. The exact critical value will depend on the specific set of incubation conditions. In general, it is preferred that, during the incubation step, the pH of the fermentation broth is maintained within the range of 4.5 to 8.0, preferably within the range of 4.8 to 6.5, more preferably within the range of 5.0-6, e.g. 5.5, in order to prevent Inhibition of lactate production. Inhibition of lactate production is considered to have occurred when the amount of lactate produced in a (batch) fermentation does not increase by more than about 3% upon further incubation for a period of up to about twelve hours under the same conditions. This definition presumes that sufficient nutrients for lactate production are still available in the fermentation broth and applies to both batch and continuous operations.

As mentioned before, prevention of the pH drop to below the critical value is accomplished by adding an alkalization agent comprising alkaline potassium salts. Alkalization, as used herein, refers to the effect of lowering the amount of acid in a solution to any extent and, hence, increasing the pH value. It does not imply an increase of the pH to above neutral. As such the term 'alkalization' is deemed to be synonymous to and interchangeable with 'neutralization'. The term "alkaline potassium salt" means an organic or inorganic salt of potassium, which reacts with an acid to accept hydrogen atoms and/or donate a pair of valence electrons, and, as such, can be added to the fermentation broth to increase the pH to the desired value. Examples of the alkaline potassium salts in accordance with the invention include potassium hydroxide and potassium carbonate. In a preferred embodiment of the invention the alkalization agent comprises potassium hydroxide.

In one embodiment of the invention, the process comprises addition of potassium hydroxide, especially the addition an aqueous solution containing at least 25 g/l of potassium hydroxide, preferably 50-600 g/l of potassium hydroxide.

It is envisaged that other neutralizing agents may be used in conjunction with potassium hydroxide. For example, other alkali or earth alkali metal hydroxides, such as sodium and/or potassium hydroxide, may be added in addition to KOH. It is however preferred that KOH and other alkali or earth alkali metal hydroxides are used in such relative amounts that at least 50% of the total mol amount of alkali and earth alkali metal ions added is potassium, more preferably at least 60%, at least 70%, at least 80%, at least 90%, or at least 95%.

As will be understood by those of ordinary skill in the art, pH control will typically involve continuous or repeated administration of neutralizing agent. The process is preferably automated for precise control of the pH at a predetermined value.

Fermentation generally will be conducted at temperatures conventionally employed in lactic acid fermentation processes. Temperatures in the range of from 20° C. to 40° C. typically will be employed, with temperatures in the range of from 20° C. to 35° C., such as about 30° C., being preferred.

Typically, the process of the present invention results in a maximum lactate production rate in excess of 2 g/l/hr, expressed as lactate equivalents. It is within the normal skilled person's abilities to determine the maximum production rate, e.g. by plotting the lactate concentration in the ferment at various time points and determining the (first) derivative of the steepest point of the curve. The present process preferably results in a maximum production rate in the final production fermenter in excess of 2.2 g/l/hr, more preferably in excess of 2.3 g/l/hr, more preferably in excess of 2.4 g/l/hr, more preferably in excess of 2.5 g/l/hr.

Typically, the maximum lactate production rate, in accordance with the present invention, is reached within the first 15 hours after initiation of step c), more preferably within the first 14 hours, within the first 13 hours, within the first 12 hours, within the first 11 hours or within the first 10 hours after initiation of step c).

The present process typically allows for the production of a broth containing a final concentration of lactate equivalents of at least 18 g/L, preferably at least 20 g/L, more preferably at least 22 g/L, still more preferably at least 23 g/L, and most preferably at least 24 g/L, e.g. 25 g/L.

Under the conditions described herein, production-scale fermentations can be performed with a duration typically varying between 10-24 hours, although the invention is not particularly limited in this respect.

The incubation can be performed using standard equipment for batch and/or continuous processing. Typically the process is performed in a (standard) production fermentor comprising a vessel having a volume of at least 250 L, at least 500 L or at least 1000 L.

In a preferred embodiment of the invention, the process is carried out in a batch-wise fashion. In a batch process according to this invention, the lactate content of in the fermentation broth will gradually increase provided the pH drop is prevented by the addition of the one or more alkalization agents. Still, at some point the "limiting lactate concentration" may be reached, which is the lactate concentration (concentration of undissociated and dissociated lactic acid) at which, under a given set of incubation conditions (pH, nutrient medium, temperature, degree of aeration), further lactate production is inhibited. In other words, growth and/or lactate material production may stop due to the accumulation of one or more fermentation products as well as in response to the pH drop resulting from the production of fermentation products, i.e. the fermentation reaction has a self limiting point for the given set of incubation conditions. The present inventors established that the nisin content typically reaches its maximum before the fermentation reaction has reached the self-limiting point and may decrease if fermentation is continued beyond said point. In the present process, the incubation step is typically stopped before the point where the concentration of lactate equivalents reaches 25 g/L, preferably 24 g/L, more preferably 23 g/L, more preferably 22 g/L. Preferably, the incubation step is allowed to proceed to the point where the concentration of lactate equivalents exceeds 15 g/L, more preferably 17 g/l, more preferably 18 g/L, more preferably 19 g/L, most preferably 20 g/l. The present process typically results in the production of a broth containing a final concentration of nisin of at least 1000 IU/ml, preferably at least 2000 IU/ml, and more preferably at least 2500 IU/ml., e.g. about 3000 IU/ml.

In a preferred embodiment of this invention, the fermentation process is stopped by the addition to the fermentation broth of an amount of acid, in particular lactic acid, sufficient to stop lactate production. A process is accordingly provided as defined in the foregoing, wherein step c) is followed by a step d1) comprising adding an amount of acid to reduce the pH of the fermented broth to below 6, preferably to below 5.5, preferably to below 5, e.g. to 4.7. In a particularly preferred embodiment said acid is lactic acid. The lactic acid will typically be added in concentrated or dilute liquid form, such in the form of an aqueous solution having a lactic acid content of at least 100 g/l, although the invention is not particularly limited in this respect. This step of acidification of the fermentation broth by the addition of acid has been found to significantly improve the overall nisin yield and/or to improve the nisin stability during subsequent treatments involving heating of the composition.

After incubation of the inoculated nutrient medium for a period sufficient to reach the desired lactate and/or nisin levels, the fermentation broth obtained is typically subjected to a further treatment in order to inactivate the lactic acid bacteria. Hence, a process is provided as defined herein before, comprising the additional step e) of subjecting the fermentation broth obtained after step c) or d) is heated to a temperature of at least 40° C., at least 45° C., or at least 50° C., for a period of at least 20, at least 30, at least 40 or at least 50 minutes, so as to inactivate the lactic acid bacteria.

The fermentation broth obtained using the present invention can be processed into a suitable product formulation simply by removing water, so as to obtain a concentrate. The lactate will be present mainly as the potassium salt and the present inventors have established that these ferments can be concentrated to particularly high level without the problem of salts crystallizing out of the product. The present inventors, furthermore, found that processing of the ferment into a concentrated form in accordance with this embodiment, gave particularly advantageous results in terms of the quality of the resulting product, especially in terms of (final) nisin activity and/or organoleptic properties. Hence, in an embodiment of the invention, a process is provided as described herein before, comprising the additional step e) of concentrating the ferment obtained in step c), d1) or d2) to a concentrate having a dry solids content of at least 50 wt. %, preferably at least 55 wt. %, more preferably at least 60 wt. %. Any conventional process can be used to perform step e). In a preferred embodiment step e) is performed by subjecting the ferment obtained in step c), d1) or d2) to an environment of above-ambient temperatures, typically to an environment of 55-70° C., and, preferably, reduced pressure, e.g. at a pressure of 190-250 mbar. For performing this step conventional equipment can be used that one of average skill is well-acquainted with.

In one embodiment, following step e), the concentrate is quickly cooled to a temperature of below 40° C., preferably below 30° C., more preferably below 20° C., more preferably to a temperature of below 10° C. The present inventors established that this step significantly aids to the quality of the resulting product, especially the (final) nisin activity and/or the organoleptic properties, e.g. compared to products that are not quickly cooled after step e). An embodiment of the invention is accordingly provided comprising a step f) wherein the concentrate obtained in step e) is cooled to a temperature of below 40° C., preferably below 30° C., more preferably below 20° C., more preferably to a temperature of below 10° C., typically by placing it in an environment of below ambient temperatures for a period sufficient to accomplish the above recited lowering of the temperature. In a particularly preferred embodiment this step comprises placing the composition in a cooling or refrigerating apparatus operated at a temperature of less than 20° C., less than 15° C. or less than 10° C. Preferably, during this step, the concentrated liquid is agitated in order to avoid accumulation of material on parts of the equipment.

Owing to the use of an alkaline potassium salt as the alkalization agent, the present invention allows for the production of ferments, including dairy based ferments, that do not need any clarification processing or other type of processing aimed at the removal of certain (solid) components from the fermentation broth in order to obtain an acceptable food-grade preservative product. Hence, in a preferred embodiment of the present invention, a process as defined herein before is provided, wherein the fermentation broth is not subjected to a processing step wherein dissolved or non-dissolved solid matter is removed from the fermented broth following step c), i.e. regardless of the application of the optional steps d), e) and/or f).

Another aspect of the invention, concerns a lactate ferment product, especially a concentrate, obtainable by the process as defined herein above. The use of the alkaline potassium salt in accordance with this invention results in a product containing substantial amounts of lactate in potassium salt form, which confers particularly advantageous properties to the ferment.

In a particularly preferred embodiment of the invention, a concentrate of the invention contains lactate and potassium cations in a molar ratio of 1/0.5 or less, preferably 1/0.6 or less, 1/0.7 or less 1/0.8 or less or 1/0.9 or less, e.g. 1/1. Preferably is above 1/1.5.

As will be understood from the foregoing lactate ferment product typically takes the form of a concentrate, which offers several generally recognized advantages over powder form products. Hence, in a preferred embodiment of the invention, a lactate ferment product is provided as described here above, wherein the lactate ferment product has a water activity of below 0.9, more preferably of below 0.8, most preferably below 0.7. In a particularly preferred embodiment of the invention, a concentrate of the invention contains at least 30% (w/v) potassium lactate, more preferably at least 30% (w./v), at least 35% (w./v), at least 40% (w./v), at least 45% (w/v) or at least 50% (w/v).

In a particularly preferred embodiment of the invention, the lactate ferment product contains at least 25 wt. % of lactate, on the basis of dry solids weight, more preferably at least 40 wt. %, most preferably at least 50 wt. %. As will be understood, this includes all forms of lactate, including free lactic acid as well as lactate containing salts, especially potassium lacatate.

In a particularly preferred embodiment, as will be understood from the foregoing, the concentrate of the invention contains appreciable levels of nisin. Hence, in a preferred embodiment of the invention, a concentrate as defined herein before is provided containing at least. 0.10 mg nisin per g of dry matter, more preferably at least 0.20 mg nisin per g of dry matter, most preferably at least 0.25 mg nisin per g of dry matter. It is to be understood that nisin actually denotes several nisin variants, such as nisin A and nisin Z, which differ in their amino acid sequence, typically only by a single amino acid. The most common variant being nisin A. The type of nisin produced will depend solely on the choice of the bacterial strain used for fermentation. The strains preferred in the context of the present invention will typically produce nisin A. Hence, the nisin is preferably nisin A. The recited amounts of nisin, as will be understood by those of average skill, apply equally to all nisin variants. Furthermore, it is to be noted that herein it is assumed that 1 microgram of nisin equals 40 IU. Hence the preferred levels of nisin correspond to activities of at least 400 IU, at least 800 IU and at least 1000 IU, all per g of dry matter, respectively.

Furthermore, as will be understood from the foregoing, the concentrate is characterized by relatively low sodium content. Hence, in a preferred embodiment of the invention, a lactate ferment product as defined herein before is provided, containing less than 3000 mg sodium per kg of dry matter, preferably less than 2500 mg sodium per kg of dry matter, more preferably less than 2000 mg of sodium per kg of dry matter.

Further aspects of the present invention concern the use of a lactate ferment product as defined in any of the foregoing for the preservation of an alimentary product, especially a food product or a beverage, more in particular a product selected from the group consisting of processed and natural cheeses, cooked meats, canned foods, seafoods, alcoholic beverages, non-alcoholic beverages, dairy deserts, dairy drinks/liquids, prepared meals, salads, dressings, sauces, flour based products, liquid egg products, etc.; and to methods of preserving such alimentary products comprising the step of incorporating therein or applying thereon a lactate ferment product as defined in any of the foregoing. The lactate ferments of the invention are particularly useful in the preservation against spoilage by a microorganism, especially a microorganism selected from the group consisting of *Listeria* spp, *clostridium* spp, lactic acid bacteria and *bacillus* spp. It is within the purview of those of ordinary skill in the art to determine the most appropriate dosages for optimal protection against spoilage while avoiding negative impact on other quality aspects of the alimentary product, especially organoleptic properties and salt content. As explained before, the present lactate ferment products can be applied in relatively high dosages without negative impact on organoleptic properties and salt content.

Thus, the invention has been described by reference to certain embodiments discussed above. It will be recognized that these embodiments are susceptible to various modifications and alternative forms well known to those of skill in the art.

Many modifications in addition to those described above may be made to the structures and techniques described herein without departing from the spirit and scope of the invention. Accordingly, although specific embodiments have been described, these are examples only and are not limiting upon the scope of the invention.

Furthermore, for a proper understanding of this document and in its claims, it is to be understood that the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

EXAMPLES

Example 1 Fermentation

Batch flasks (2 L) are used as reactors for fermentation. This reactor is sterilized empty for 20 min at 121° C. All cultivations are performed aseptically. Whey powder 5% w/w and Yeast extract 0.2% w/w (based on dry weight) is used as a nutrient medium (pasteurized for 30 min at 80° C. inside the reactor). KOH 25% w/w was used as alkalization agent to control the pH, which is kept at around 5.5. The fermentation temperature is 30° C.

A first batch flask with whey powder and yeast extract medium is inoculated from a glycerol stock of *Lactococcus lactis* ATCC 11454 and incubated overnight at 30° C. The inoculum was 2.5% w/w. During exponential growth phase ferment from the first batch flask is transferred as inoculum for the next 2 L batch flask reactor with whey powder 5% w/w and Yeast extract 0.2% w/w ran under the same conditions. The fermentation in the second reactor is stopped when the lactate concentration reaches 25 g/l. Around 10 ml of lactic acid (80% dry solids) is sufficient to lower the pH to 4.7. The reactor is kept at 50° C. for 1 hour for inactivation. The final nisin content is around 3000 IU/ml.

The ferment from the second batch flask reactor is subjected to evaporation in order to produce a concentrate (approximately 50% (w/v) potassium lactate). The concentrate is sufficiently storage stable. The incorporation of the concentrate in various alimentary products at effective dosages results in organoleptic properties that are generally favoured over those obtained with prior art nisin ferments.

Example 2 Fermentation with Activated Inocculum

In a variant of the above process, a much stronger inoculum is created by adding enriched nutrient medium to the first reactor, by adding 0.4-1% w/w Yeast extract. This results in a quicker fermentation time in the first reactor. Using "activated" inoculum from the first reactor to start the final reactor with whey powder 5% w/w and Yeast extract 0.2% w/w, in accordance with example 1, results in a quicker fermentation time and significantly improved overall performance.

The ferment obtained in accordance with this variant is subjected to evaporation in order to produce a concentrate (approximately 50% (w/v) potassium lactate). The concentrate is sufficiently storage stable. The incorporation of the concentrate in various alimentary products at effective dosages results in organoleptic properties that are generally favoured over those obtained with prior art nisin ferments.

Example 3 Nisin Stability

Nisin containing lactic acid ferment is produced following the procedure of example 2. The final product was prepared from the raw ferment and concentrated by evaporation to a 55° Brix, heat treated at 75° C. for 15 sec and aseptically packaged into 2 kg bags. Final pH of the concentrated product was 5.4. Part of the material was taken separately and the pH was adjusted to 4.7 by adding hydrochloric acid. The samples were placed in plastic vials and stored for stability tests along with the original material.

For stability tests both samples (pH 5.4 and PH 4.7) were stored at temperatures of 4° C., room temperature (25° C.) and 40° C. Measurements of nisin activity were done at 0.5, 1, 2, 3, 4, 5, 6, 9, 12 months for all temperatures and activity decrease was determined by comparison the reference sample stored at −28° C. (to reduce error variation within measurements).

Figure 2:
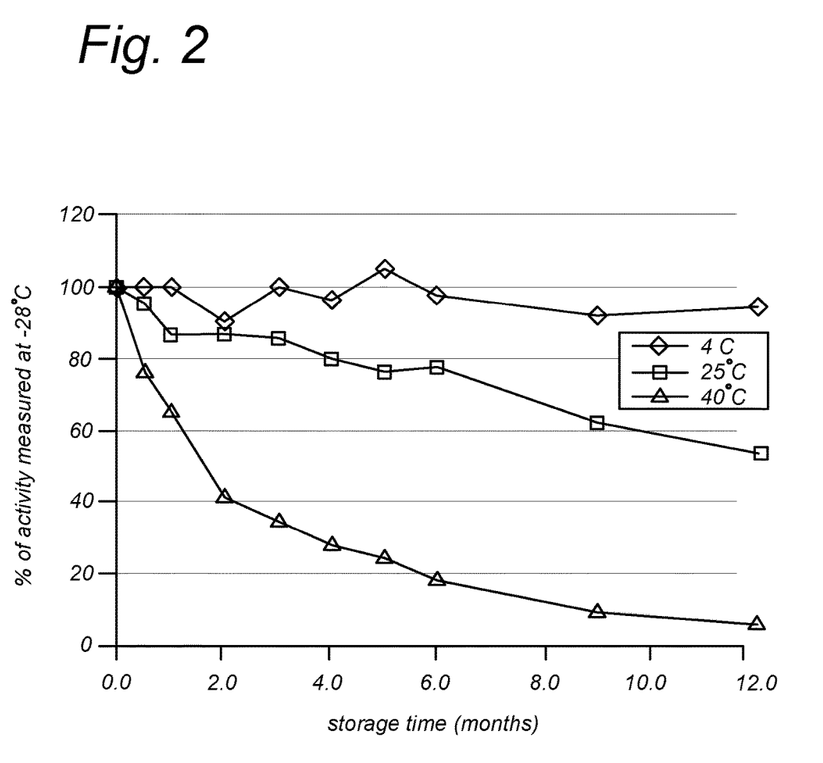

Results are shown in FIGS. 1 and 2. FIG. 1 is a graph depicting the decrease of nisin activity of the original samples (pH=5.4) in time (% of activity measured at −28° C.) when stored at 4° C., 25° C. and 40° C. FIG. 2 is a graph depicting the decrease of nisin activity of adjusted samples (pH=4.7) in time (% of activity measured at −28° C.) when stored at 4° C., 25° C. and 40° C. The results as shown in FIGS. 1 and 2 indicate that the nisin activity is strongly impacted by temperature and decreases substantially as the temperature increases. The pH difference between the samples appears to have a significant effect on nisin stability, particularly when stored at room temperature (25° C.). At storage temperatures of 4 and 25° C. the concentrates have a considerable shelf life of at least 6 months, during which the deterioration of the nisin activity is within acceptable limits.

The invention claimed is:

1. A process of producing a nisin-containing lactate ferment, comprising the consecutive steps of:
   (a) innoculating a nutrient medium comprising a solution of a fermentable substrate and a nitrogen source in an aqueous medium with nisin-producing lactic acid bacteria;
   (b) incubating the inoculated nutrient medium under conditions favorable to the growth and/or metabolic activity of the nisin-producing lactic acid bacteria, for a period sufficient to produce a fermentation broth containing at least 10 g/l of lactate equivalents and/or at least 1000 IU/ml of nisin equivalent activity, during which period the pH of the fermentation broth is controlled by continuous or repeated addition of an alkalization agent comprising an alkaline potassium salt; and
   (c) concentrating the fermentation broth obtained in step (b) to a dry solids content of at least 50 wt. %.

2. The process according to claim 1, wherein the pH of the fermentation broth is maintained between 4.5 to 8.0.

3. The process according to claim 1, wherein the pH of the fermentation broth is maintained between 5.0 to 6.0.

4. The process according to claim 1, further comprising inactivating the lactic acid bacteria by subjecting the fermentation broth to a temperature of at least 40° C. for a period of at least 10 minutes.

5. The process according to claim 1, further comprising (d) cooling the concentrate to a temperature of below 40° C.

6. The process according to claim 1, wherein the nutrient medium comprises a dairy product.

7. The process according to claim 1, wherein the nutrient medium comprises whey.

8. The process according to claim 1, wherein the method does not include removing non-dissolved matter from the fermentation broth.

9. The process according to claim 1, wherein the inoculated medium comprises an activated nisin-producing lactic acid bacteria.

10. The process according to claim 9, wherein the fermentation broth comprises more than 14 g/l of lactate equivalents.

11. The process according to claim 1, further comprising acidifying the fermentation broth by the addition of an acid in an amount sufficient to reduce the pH of the fermentation broth to below 4.8.

12. The process according to claim 11, wherein the acid is lactic acid.

* * * * *